US010316332B2

(12) United States Patent
Fujii (10) Patent No.: US 10,316,332 B2
(45) Date of Patent: *Jun. 11, 2019

(54) CELL FOR IMMUNOTHERAPY, INCLUDING MODIFIED NUCLEIC ACID CONSTRUCT ENCODING WILMS TUMOR GENE PRODUCT (71) Applicant: RIKEN, Saitama (JP)

(72) Inventor: Shin-ichiro Fujii, Yokohama (JP)

(73) Assignee: RIKEN, Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/906,930

(22) Filed: Feb. 27, 2018

(65) Prior Publication Data
US 2018/0195087 A1 Jul. 12, 2018

Related U.S. Application Data (63) Continuation-in-part of application No. 15/708,900, filed on Sep. 19, 2017, now abandoned, which is a continuation of application No. 14/235,333, filed as application No. PCT/JP2012/069377 on Jul. 30, 2012, now Pat. No. 9,783,821.

(30) Foreign Application Priority Data

Jul. 29, 2011 (JP) ................. 2011-167796

(51) Int. Cl.
C12N 15/85 (2006.01)
C07K 14/82 (2006.01)
A61K 39/00 (2006.01)
C07K 14/47 (2006.01)

(52) U.S. Cl.
CPC .......... *C12N 15/85* (2013.01); *A61K 39/0011* (2013.01); *C07K 14/4748* (2013.01); *C07K 14/82* (2013.01); *A61K 2039/5152* (2013.01); *A61K 2039/5156* (2013.01); *C07K 2319/00* (2013.01); *C07K 2319/50* (2013.01)

(58) Field of Classification Search
None
See application file for complete search history.

(56) References Cited

U.S. PATENT DOCUMENTS

| 2003/0072767 A1 | 4/2003 | Gaiger |
| 2010/0233215 A1 | 9/2010 | Fujii |
| 2011/0190384 A1 | 8/2011 | Sugiyama |
| 2011/0280895 A1 | 11/2011 | Fujii |
| 2013/0189302 A1 | 7/2013 | Fujii |
| 2014/0179004 A1 | 6/2014 | Fujii |

FOREIGN PATENT DOCUMENTS

| EP | 2308987 | 4/2011 |
| WO | 2007/097370 | 8/2007 |
| WO | 2007119564 | 10/2007 |
| WO | 2009-046974 | 4/2009 |
| WO | 2010/061930 | 6/2010 |
| WO | 2011/059835 | 5/2011 |

OTHER PUBLICATIONS

Wagner, K. et al., Gene, 2003, vol. 305: pp. 217-223.*
Search Report for PCT/JP2012/069377 dated Sep. 4, 2012.
Shastri, N., et al., "Major histocompatibility class I molecules can present cryptic translation products to T-cells", J. Biol. Chem., Jan. 20, 1995, vol. 270, No. 3, pp. 1088-1091.
Ja Kyte et al., "Phase I / II trial of melanoma therapy with dendritic cells transfected with autologous tumor-mRNA", Cancer Gene Therapy, vol. 13 (2006), pp. 905-918.
LJ Mu, et al., "Immunotherapy with allotumour mRNA-transfected dendritic cells in androgen-resistant prostate cancer patients", British Journal of Cancer, vol. 93 (2005), pp. 749-756.
Zhen Su, et al., "Telomerase mRNA—Transfected Dendritic Cells Stimulate Antigen-Specific CD8+ and CD 4+ T Cell Responses in Patients with Metastatic Prostate Cancer", The Journal of Immunology, vol. 174 (2005), pp. 3798-3807.
Axel Heiser, et al., "Autologous dendritic cells transfected with prostate-specific antigen RNA stimulate CTL responses against metastatic prostate tumors", Journal of Clinical Investigation, vol. 109, No. 3, Feb. 2002, pp. 409-417.
Smita K. Nair, et al., "Induction of cytotoxic T cell responses and tumor immunity against unrelated tumors using telomerase reverse transcriptase RNA transfected dendritic cells", Nature Medicine, vol. 6, No. 8, Sep. 2000, pp. 1011-1017.
Condon C., et al., "DNA-based immunization by vivo transfection of dendritic cells", Nat. Med. vol. 2, Oct. 1996, pp. 1122-1128 (Abstract Only).
David Boczkowski et al., "Dendritic Cells Pulsed with RNA are Potent Antigen-presenting Cells in Vitro and in Vivo", J. Exp. Med., vol. 184, Aug. 1996, pp. 465-472.
Silk, Jonathan D. et al., "Utilizing the adjuvant properties of CD1d-dependent NKT cells in T cell-mediated immunotherapy", The Journal of Clinical Investigation, vol. 114, No. 12, Dec. 2004, pp. 1800-1811.

(Continued)

*Primary Examiner* — Michael D Burkhart
(74) *Attorney, Agent, or Firm* — Casimir Jones, SC; Robert A. Goertz (57) ABSTRACT

A cell for immunotherapy of the present invention includes a nucleic acid encoding a Wilms tumor 1 gene product or a fragment of the Wilms tumor 1 gene product, wherein the nucleic acid including (i) a region encoding a fragment of the Wilms tumor 1 gene product, the fragment being indicated by positions 194 to 493 of amino acid sequence of SEQ ID NO:1 or by positions corresponding to the positions 194 to 493 of amino acid sequence corresponding to SEQ ID NO:1 and (ii) only one AUG as a functional start codon, connected to a 5' terminal side of the region via 3m (m is 124-192) bases intervening between the AUG as the functional start codon and the 5' terminal side of the region, and a nucleic acid encoding CD1d, wherein the cell has been loaded with a glycolipid recognized by antigen receptor of NKT cell.

3 Claims, 2 Drawing Sheets
Specification includes a Sequence Listing.

(56) References Cited

OTHER PUBLICATIONS

Hermans, Ian F. et al., "NKT Cells Enhance CD4+ and CD8+ T cell Responses to Soluble Antigen In Vivo through Direct Interaction with Dendritic Cells", The Journal of Immunology, vol. 171 (2003), pp. 5140-5147.

Fais, Franco et al., "CD1d is Expressed on B-Chronic Lymphocytic Leukemia Cells and Mediates α-Galactosylceramide Presentation to Natural Killer T Lymphocytes", Int. J. Cancer, vol. 109 (2004), pp. 402-411.

Metelitsa, Leonid S. et al., "Human NKT Cells Mediate Antitumor Cytotoxicity Directly by Recognizing Target Cell CD1d with Bound Ligand or Indirectly by Producing IL-2 to Activate NK Cells", The Journal of Immunology, vol. 167 (2001), pp. 3114-3122.

Fujii, Shin-ichiro et al., "Detection and activation of human Vα24+ natural killer T cells using α-galactosyl ceramide-pulsed dendritic cells", Journal of Immunological Methods, vol. 272 (2003), pp. 147-159.

Fujii, Shin-ichiro et al., "The Linkage of Innate to Adaptive Immunity via Maturing Dendritic Cells In Vivo Requires CD40 Ligation in Addition to Antigen Presentation and CD80/86 Costimulation", J. Exp. Med., vol. 199, No. 12, Jun. 21, 2004, pp. 1607-1618.

Fujii, Shin-ichiro et al., "Activation of Natural Killer T Cells by α-Galactosylceramide Rapidly Induces the Full Maturation of Dendritic Cells In Vivo and Thereby Acts as an Adjuvant for Combined CD4 and CD8 T Cell Immunity to a Coadministered Protein", J. Exp. Med., vol. 198, No. 2, Jul. 21, 2003, pp. 267-279.

Fujii, Shin-ichiro et al., "Prolonged IFN-γ-producing NKT response induced with α-galactosylceramide-loaded DCs", Nature Immunology, vol. 3, No. 9, Sep. 2002, pp. 867-874.

English translation of the International Preliminary Report on Patentability (Chapter 1) of PCT Application No. PCT/JP2012/069377 dated Feb. 13, 2014.

Bruening, W. & Pelletier, J. et al., "A non-AUG translational initiation event generates novel WT1 isoforms", The Journal of Biological Chemistry, 1996, vol. 271, No. 15, pp. 8646-8654.

Office Action for Australian Patent Application No. 2012291101, dated Feb. 27, 2015.

European Search Report, European Patent Application No. 12820579.6, dated Mar. 20, 2015.

Non-Final Rejection, U.S. Appl. No. 14/235,333, dated Nov. 4, 2015.

Non-Final Rejection, U.S. Appl. No. 14/235,333, dated May 18, 2016.

Final Rejection, U.S. Appl. No. 14/235,333, dated Nov. 30, 2016.

Final Rejection, U.S. Appl. No. 14/235,333, dated Feb. 24, 2017.

Non-Final Rejection, U.S. Appl. No. 15/708,900, dated Jul. 13, 2017.

\* cited by examiner

FIG. 2

CELL FOR IMMUNOTHERAPY, INCLUDING MODIFIED NUCLEIC ACID CONSTRUCT ENCODING WILMS TUMOR GENE PRODUCT

The present application is a continuation-in-part of U.S. patent application Ser. No. 15/708,900, filed Sep. 19, 2017, which is a continuation of U.S. patent application Ser. No. 14/235,333, filed Jan. 27, 2014, now U.S. Pat. No. 9,783,821, which is a Section 371 U.S. national stage entry of International Patent Application No. PCT/JP2012/069377, International Filing Date Jul. 30, 2012, which claims the benefit of Japanese Patent Application No. 2011-167796, filed Jul. 29, 2011, the contents of which are incorporated by reference in their entireties.

TECHNICAL FIELD

The present invention relates to a nucleic acid construct encoding a Wilms tumor gene product or a fragment of the Wilms tumor gene product. The present invention further relates to a cell into which the nucleic acid construct is introduced so that an expression level of the Wilms tumor gene product or the fragment of the Wilms tumor gene product is remarkably enhanced therein.

BACKGROUND ART

Antitumor effects of an NKT cell which have been known so far include (i) a direct effect on a tumor and (ii) an indirect effect on a tumor via maturation of a dendritic cell (adjuvant effect). As an immunotherapy using the NKT cell, an immunotherapy involving administration of a dendritic cell presenting a tumor antigen has been known, and studies for clinical application of such the immunotherapy have been conducted (Non-Patent Literatures 1 through 7). Further, an antigen-specific immunotherapy using a dendritic cell into which mRNA encoding a tumor antigen is introduced has been already established and clinically applied (Non-Patent Literatures 8 through 15). In order to introduce, into a cell material to be used, an antigen for immune induction in such immunotherapies, it is simple and easy to use an expression vector or the like. However, in a case where the expression vector is introduced into the cell in such an immunotherapy, that immunotherapy may be regarded as a gene therapy and application range thereof may be limited due to regulations. As a measure for avoiding this, introduction of RNA into a dendritic cell has been considered. However, this involves problems of a low introduction efficiency of RNA and a low expression level of a tumor antigen in the dendritic cell. In order to improve therapeutic effects of these immunotherapies, attempts to try various combinations with adjuvants have been made.

Another immunotherapy for a tumor is a peptide therapy involving use of a plurality of epitopes contained in a WT1 protein encoded by a Wilms tumor gene (Wilms tumor 1: WT1).

Meanwhile, the inventors of the subject application have developed unique immunotherapies (Patent Literatures 1, 2, etc.). Disclosed in Patent Literature 1 are (i) an abnormal cell which is isolated from a patient and has, on its surface, CD1d presenting an NKT cell ligand and (ii) a method for producing the cell (Patent Literature 1). This cell is capable of inducing both activation of NKT cells and tumor-specific immune response of T-cells. Disclosed in Patent Literature 2 are (i) an allo-cell which is not derived from a patient and has, on its surface, CD1d presenting an NKT cell ligand and in which a disease-specific antigen is expressed and (ii) a method for producing the cell. This allo-cell is capable of exhibiting immune inducibility similar to that of the cell disclosed in Patent Literature 1 without being isolated from a patient. Such the immunotherapies are expected to be applied to various antitumor immunotherapies for leukemia etc.

CITATION LIST

Patent Literatures

Patent Literature 1
WO 2007/097370 (Publication Date: Aug. 30, 2007)
Patent Literature 2
WO 2010/061930 (Publication Date: Jun. 3, 2007)

Non-Patent Literatures

Non-Patent Literature 1
Nat. Immunol. 3, 867-874 (2002).
Non-Patent Literature 2
J. Immunol. Meth. 272, 147-159 (2003).
Non-Patent Literature 3
J. Exp. Med. 198, 267-279 (2003).
Non-Patent Literature 4
J. Exp. Med. 199, 1607-1618 (2004).
Non-Patent Literature 5
J. Immunol. 167, 3114-3122 (2001).
Non-Patent Literature 6
Int. J. Cancer 109, 402-11 (2004).
Non-Patent Literature 7
J. Immunol. 171, 5140-5147 (2003).
Non-Patent Literature 8
J. Clin. Invest. 114, 1800-11 (2004).
Non-Patent Literature 9
J. Exp. Med. 184:465-472 (1996).
Non-Patent Literature 10
Nat. Med. 2:1122-1128 (1996).
Non-Patent Literature 11
Nat. Med. 6:1011-1017 (2000).
Non-Patent Literature 12
J. Clin. Invest. 109:409-417 (2002).
Non-Patent Literature 13
J. Immunol. 174:3798-3807 (2005).
Non-Patent Literature 14
Br. J. Cancer 93:749-756 (2005).
Non-Patent Literature 15
Cancer Gene Ther. 13:905-918 (2006).

SUMMARY OF INVENTION

Technical Problem

The immunotherapies developed by the inventors of the subject application can improve therapeutic effect in combination with an adjuvant, as with the conventional immunotherapies. However, the inventors of the present invention found that, as the immunotherapies are cell-based immunotherapies and a cell itself to be administered is a target to be attacked by an immune system of a patient, an increase in an expression level of the tumor antigen protein therein greatly contributes to an increase in efficiency of the immune induction.

Solution to Problem

The present invention includes the following features; A cell for immunotherapy, including: a nucleic acid construct encoding a Wilms tumor gene product or a fragment of the Wilms tumor gene product, the nucleic acid construct including (i) a region encoding a fragment of the Wilms tumor gene product, the fragment being indicated by positions 194 to 493 of SEQ ID NO: 1 or by positions corresponding to the positions 194 to 493 of a sequence corresponding to SEQ ID NO: 1 and (ii) only one AUG as a functional start codon, connected to a 5' terminal side of the region via 3m (m is 0 or a positive integer) bases intervening between the 5' terminal side of the region and the AUG as the functional start codon.

Advantageous Effects of Invention

According to the present invention, it is possible to induce the increased immune response in a patient to tumor cells having WT1 antigen.

DESCRIPTION OF EMBODIMENTS

[Cell for Immunotherapy of the Present Invention]

The present invention provides a cell for immunotherapy (hereinafter, simply referred to as a "cell of the present invention") which cell contains a nucleic acid construct encoding a Wilms tumor gene product or a fragment of the Wilms tumor gene product. The nucleic acid construct includes (i) a region encoding a fragment of the Wilms tumor gene product, the fragment being indicated by positions 194 to 493 of SEQ ID NO: 1 or by positions corresponding to the positions 194 to 493 of a sequence corresponding to SEQ ID NO: 1 and (ii) only one AUG as a functional start codon, connected to a 5' terminal side of the region via 3m (m is 0 or a positive integer) bases intervening between the 5' terminal side of the region and the AUG as the functional start codon.

The cell of the present invention can be such a dendritic cell that is for immunotherapy including administration of a tumor antigen-presenting dendritic cell and is derived from a living body to which the cell is to be administered. As to the immunotherapy using a dendritic cell, various publicly known literatures can be referred to. Therefore, detailed description of the immunotherapy using a dendritic cell is omitted in the present specification.

Therefore, the following description will discuss a cell particularly preferable as the cell of the present invention. The cell further contains mRNA encoding CD1d, for the purpose of application to the immunotherapies developed by the inventors of the present invention (see WO 2007/097370 and WO 2010/061930). Further, the cell is preferably bound to a glycolipid, recognized by an antigen receptor of an NKT cell, via the CD1d existing on a surface of the cell. Thus, the glycolipid is presented by the CD1d on the surface of the cell of the present invention. Therefore, in a case where the cell is administered to a living body, the cell of the present invention is efficiently attacked by an NKT cell. With this damage, the WT1 gene product or the fragment of the WT1 gene product expressed from the nucleic acid construct of the present invention is processed to a peptide fragment. For example, a surrounding dendritic cell takes up the peptide fragment, and then presents to a T cell the peptide fragment and a major histocompatibility antigen (MHC) class II molecule, so that the T cell is activated. At the same time, the NKT cell which has damaged the cell of the present invention is activated by the surrounding dendritic cell which has taken up the peptide fragment. That is, administration of the cell of the present invention causes innate immunity and acquired immunity which is dependent on a tumor-specific antigenic peptide (peptide fragment). Cells having such features are generally called as "artificial adjuvant vector cells (aAVC)".

The CD1d is an MHC-like molecule which presents a glycolipid as described above. The CD1d is expressed in antigen-presenting cells (such as a dendritic cell) and epithelial cells of specific tissues (such as an intestinal canal and a liver) and in some tumor cells (such as a solid tumor cell and a leukemia cell) and virus-infected cells.

Examples of the glycolipid recognized by the antigen receptor of the NKT cell include α-GalCer (α-galactsylceramide), α-C-GalCer (α-C-galactsylceramide), iGB3 (isoglobotrihexosylceramide), GD3 (ganglioside 3), GSL-1 (α-linked glucronic acid), and GSL-1'SA (galacturonic acid). Among those glycolipids, α-GalCer or α-C-GalCer is preferable.

Further, the cell of the present invention is preferably an established cell line. The established cell line is high in proliferation efficiency and gene introduction efficiency, as compared with a cell or the like obtained from a living body. Therefore, from the established cell line, it is possible to stably prepare a large amount of cells. The established cell line can be a mammal-derived cell. In view of clinical application to a human, the cell of the present invention is preferably a human-derived cell, especially, a cell derived from a normal cell of a human. Note that, in a case of application to a pet animal (such as a dog and a cat), a cell derived from an animal species which is a target of administration can be used. Alternatively, a human-derived cell can be used therefor as with the application to a human.

[Nucleic Acid Construct of the Present Invention]

Further, the present invention provides a nucleic acid construct encoding a Wilms tumor gene product or a fragment of the Wilms tumor product. As described above, the nucleic acid construct includes (i) a region encoding a fragment of the Wilms tumor gene product, the fragment being indicated by positions 194 to 493 of SEQ ID NO: 1 or by positions corresponding to the positions 194 to 493 of a sequence corresponding to SEQ ID NO: 1 and (ii) only one AUG as a functional start codon, connected to a 5' terminal side of the region via 3m (m is 0 or a positive integer) bases intervening between the 5' terminal side of the region and the AUG as the functional start codon.

Each of the terms "Wilms tumor gene product" and "fragment of the Wilms tumor gene product" used in the present specification means (i) a polypeptide represented by an amino acid sequence identical to that of a wild type protein encoded by a Wilms tumor gene (Wilms tumor 1: WT1) (hereinafter, referred to as a "polypeptide identical to a wild type protein"), (ii) a polypeptide represented by an amino acid sequence substantially identical to that of the wild type protein (hereinafter, referred to as a "polypeptide similar to a wild type protein"), or (iii) a polypeptide containing a WT1-derived peptide, which is known as a tumor-specific antigen peptide (hereinafter, referred to as a "tumor-specific polypeptide").

Note, here, that the polypeptide identical to a wild type protein is a polypeptide encoded by cDNA of a publicly-known WT1 gene. The WT1 gene has various variants. Among the variants, cDNA encoding a polypeptide whose full length is the longest is represented by a sequence of SEQ ID NO: 3 (GenBank# NM. 024426). What is represented by this sequence is known as Variant D of WT1. Currently, it is known that WT1 has Variants A through D (A: GenBank# NM 000378, B: GenBank# NM 024424, C: GenBank# NM 024425, D: GenBank# NM 024426). The polypeptide identical to a wild type protein in the present specification means, for example, a polypeptide encoded by a polynucleotide represented by a sequence of SEQ ID NO: 3 in which substitution, deletion, or addition each being observed in various variants is optionally introduced into a corresponding position thereof. Note that the WT1 gene is known to express two proteins having respective different lengths. Therefore, the term "polypeptide identical to a wild type protein" includes a polypeptide which has or does not have the mutation observed in the variants as those described above and which is represented by an amino acid sequence identical to those of two proteins having the respective different lengths.

On the other hand, in comparison with the polypeptide identical to a wild type protein in terms of an amino acid sequence, the polypeptide similar to a wild type protein is a polypeptide having an amino acid sequence with 90% or more, preferably 95% or more, more preferably 99% or more identity to that of the polypeptide identical to a wild type protein. Furthermore, the polypeptide similar to a wild type protein is a polypeptide having a region corresponding to a tumor-specific antigen peptide into which a mutation being known not to impair immune inducibility, being known to improve immune inducibility, or being known to change an applicable type of a human leukocyte antigen is introduced.

Examples of the mutation include a mutation described in WO 05/045027. The mutation is substitution of an amino acid at position 1, 4, 6, or 9 from a C-terminal of a peptide consisting of nine amino acid residues with another amino acid. In accordance with WO 05/045027, an amino acid residue can be substituted with another amino acid according to the following correspondence: An amino acid at position 1 can be substituted with any one of phenylalanine, tyrosine, tryptophan, valine, isoleucine, leucine, and methionine. An amino acid at position 4 can be substituted with any one of valine, isoleucine, leucine, methionine, aspartic acid, and glutamic acid. An amino acid at position 6 can be substituted with any one of asparagine, serine, threonine, glutamine, lysine, and aspartic acid. An amino acid at position 9 can be substituted with aspartic acid, glutamic acid, or glutamine.

Examples of the mutation further include a mutation described in WO 05/053618. According to the mutation, an amino acid at position 9 of nine amino acid residues encoded by bases corresponding to bases at positions 770 to 796 of SEQ ID NO: 3 of the present invention is substituted with leucine.

Examples of the mutation further include a mutation described in WO 07/016466. According to the mutation, an amino acid at position 9 of nine amino acid residues encoded by bases corresponding to bases at positions 770 to 796 of SEQ ID NO: 3 of the present invention is substituted with methionine.

Examples of the mutation further include two mutations described in a Response of European patent No. 1127068. According to a first one of the two mutations, an amino acid at position 2 of nine amino acid residues encoded by bases corresponding to bases at positions 770 to 796 of SEQ ID NO: 3 of the present invention is substituted with leucine. According to a second one of the two mutations, amino acids at positions 2 and 9 of nine amino acid residues encoded by bases corresponding to bases at positions 770 to 796 of SEQ ID NO: 3 of the present invention are substituted with leucine and valine, respectively.

On the other hand, in comparison with the polypeptide identical to a wild type protein in terms of an amino acid sequence of a region containing an antigen peptide, the tumor-specific polypeptide is a polypeptide having an amino acid sequence with 90% or more, preferably 95% or more, more preferably 99% or more identity to that of the polypeptide identical to a wild type protein. Furthermore, the polypeptide similar to a wild type protein is a polypeptide into which a mutation being known not to impair immune inducibility, being known to improve immune inducibility, or being known to change an applicable type of a human leukocyte antigen is introduced. Examples of the mutation include the mutations described above.

Thus, the nucleic acid construct of the present invention contains a polynucleotide encoding the polypeptide identical to a wild type protein, the polypeptide similar to a wild type protein, or the tumor-specific peptide. Therefore, in addition to the mutation in the WT1 gene as those described above, the nucleic acid construct of the present invention optionally has a conservative mutation which does not change an amino acid to be encoded.

Into the nucleic acid construct of the present invention, such a mutation is further introduced by which one or two base(s) is/are inserted into a 5' terminal side of "A" at the beginning thereof, in a case where (i) bases represented by "AUG" are generated, by any of the aforementioned mutations, at any position in a region from positions 192 to 769 of SEQ ID NO: 2 or in a region corresponding to that region of a sequence corresponding to SEQ ID NO: 2 and (ii) "A" at the beginning thereof exists at a position other than positions 191+3m (m is an integer from 1 to 192).

As used in the present specification, the term "corresponding sequence" in the descriptions referring to SEQ ID NO: 2 means a sequence of RNA corresponding to publicly-known cDNA indicating any of the various the variants of the WT1 gene as those described above, into which variants any of the various mutations can be introduced as described above. Further, the term "corresponding base" means a base specified in the "corresponding sequence" when compared with a base at position X (X is any integer) of SEQ ID NO: 2 and bases around that base. A person skilled in the art who reads the present specification would easily understand the meanings of the terms "corresponding sequence" and "corresponding base", and easily find out, in a suitably-selected "corresponding sequence" of SEQ ID NO: 2, a "corresponding base" of the base at the position X of SEQ ID NO: 2. Hereinafter, the nucleic acid construct of the present invention will be explained with reference to SEQ ID NO: 2, which is shown as a reference sequence. Further, in all the descriptions, the nucleic acid construct of the present invention is intended to be indicated by a position or a region of a base in a sequence corresponding to SEQ ID NO: 2.

In the nucleic acid construct of the present invention, a base corresponding to a base at position 191 of SEQ ID NO: 2 can be substituted with a base represented by, for example, "A", "U", or "G". It has been reported that such the substitution with any of "A", "U", and "G" can generate a codon serving as a start codon in a eukaryote. Further, in the nucleic acid construct of the present invention, any successive bases from a base corresponding to a base at position 191 of SEQ ID NO: 2 to a base at position 769 of SEQ ID NO: 2 can be deleted. This makes it possible to provide a nucleic acid construct encoding a polypeptide which contains a publicly-known tumor-specific antigen peptide as those described above.

Preferably, into the nucleic acid construct of the present invention, such a mutation is introduced that generates a region starting from three bases represented by "AUG". This mutation generates a start codon which is found in eukaryotes the most, thereby increasing the possibility that this region is recognized as a coding region. Examples of RNA contained in the nucleic acid construct to which such a mutation is introduced include the following three RNAs:

RNA (1) represented by SEQ ID NO: 2 in which a base at position 191 is substituted with "A"; RNA (2) represented by SEQ ID NO: 2 in which successive 204 bases starting from a base at position 191 are deleted; and RNA (3) containing (i) a first region in which three bases represented by "AUG" and any 3m (m is an integer of 0 (zero) or 1 to 250, more preferably 1 to 200) bases are positioned continuously in this order from a 5' terminal and (ii) a second region from position 770 to position 1663 of SEQ ID NO: 2, the first region being followed by the second region.

The RNA (1) is RNA including a region of the nucleic acid construct of the present invention which region encodes a WT1 polypeptide and has the first base being substituted with a base represented by "A". The RNA (2) is RNA including a region of the nucleic acid construct of the present invention which region encodes a WT1 polypeptide and starts from three bases represented by "AUG". The RNA (3) is RNA including (i) "AUG", (ii) 0 (zero) or 3-multiple bases positioned to follow the "AUG", and (iii) a polypeptide chain including a region identified to encode a tumor-specific antigen peptide (a region from a position 770 to a position 1663 of SEQ ID NO: 2), the "AUG" and the 0 (zero) or 3-multiple bases being added to a C-terminal of the polypeptide chain.

Further, the nucleic acid construct of the present invention is preferably the one represented by (i) SEQ ID NO: 2 in which bases at positions 1 to 100, preferably positions 1 to 150, more preferably 1 to 120, even more preferably positions 1 to 190 of SEQ ID NO: 2 are deleted or (ii) the corresponding sequence in which bases corresponding to these bases are deleted. In a case where the nucleic acid construct, having such the deletion, of the present invention is inserted into a transcription construct (described later), a protein is expressed more suitably because a distance between a promoter and a start codon is suitably adjusted therein.

Furthermore, the nucleic acid construct of the present invention preferably includes a 5' cap structure. The 5' cap structure in the nucleic acid construct of the present invention can be added in vitro or in vivo. In consideration of facilitation of purification and isolation, it is preferable that (i) transcription is carried out in vitro with the use of RNA including a region encoding a WT1 polypeptide and (ii) the 5' cap structure is then added thereto in vitro. The transcription and the addition of the 5' cap structure in vitro can be easily carried out by a method publicly known to a person skilled in the art, or with the use of a commercially available reagent or kit.

Furthermore, in order to improve stability of RNA and an expression level of a protein, it is preferable that the nucleic acid construct of the present invention further includes a polyadenylation (Poly-A) chain at its 3' terminal. The Poly-A chain can be added to the nucleic acid construct of the present invention in vitro or in vivo as with the 5' cap structure. However, for similar reasons, it is preferable that the Poly-A chain is added to the nucleic acid construct of the present invention in vitro. Similarly, the addition of the Poly-A chain can be easily carried out by a method publicly known to a person skilled in the art, or with the use of a commercially available reagent or kit.

[Polynucleotide Encoding Nucleic Acid Construct of the Present Invention, and Transcription Construct Containing the Polynucleotide]

The present invention provides a polynucleotide encoding the nucleic acid construct of the present invention as described above. The polynucleotide of the present invention includes a region of a WT1 gene encoding a WT1 gene product or a fragment of the WT1 gene product. Further, into the polynucleotide, such a mutation is introduced that corresponds to the mutation introduced into the nucleic acid construct of the present invention as described above. The polynucleotide of the present invention is particularly suitable for production of the nucleic acid construct of the present invention. In a case where the polynucleotide is used to produce the nucleic acid construct of the present invention, the polynucleotide of the present invention is incorporated into a transcription construct of the nucleic acid construct of the present invention.

As described above, the present invention also provides a transcription construct containing the polynucleotide of the present invention. The transcription construct further contains various elements which enable efficient transcription of the polynucleotide to RNA. As described above, the transcription of the nucleic acid construct of the present invention is preferably carried out in vitro. Therefore, the various elements to be contained in the transcription construct can be selected in accordance with a method, a kit, or the like for in vitro transcription. The following description will specifically discuss, as an example of the transcription construct of the present invention, a construct adapted to a commercially available kit for in vitro transcription.

The transcription construct contains a promoter which is operably linked to the polynucleotide. The promoter is applicable as long as the promoter can promote the transcription of the polynucleotide to RNA in vitro. Examples of the promoter include a T7 promoter, an SP6 promoter, and a T3 promoter. The transcription construct can further contain a transcription termination signal (that is, a terminator sequence) at a downstream of the polynucleotide. Examples of the terminator sequence include a T7 terminator, an SP6 terminator, and a T3 terminator. Note that the transcription termination signal is not necessary, in a case where transcription is carried out after the transcription construct is cut out at a downstream of the polynucleotide by use of a restriction enzyme or the like.

The transcription construct can function as a vector so as to amplify the transcription construct itself. In this case, the transcription construct can further contain a selection marker gene for selection of a cell into which the transcription construct is introduced. Examples of the selection marker gene include a gene having resistance to a conventionally known antibiotic, a gene which compensates for an auxotrophic mutation, and a gene which expresses an enzyme that catalyzes a color reaction with a reagent. In a case where the transcription construct does not have such selectivity, the transcription construct can be amplified by PCR, for example. Therefore, the transcription construct can be a linear polynucleotide chain which is amplified by PCR and which is not inserted into plasmid DNA. In this case, a primer pair is designed so that a template is amplified together with a promoter region of RNA.

In a case where a transcription construct further encoding mRNA of CD1d is prepared, the transcription construct is polycistronic or monocistronic. In a case where the transcription construct is polycistronic, the transcription construct contains one promoter at an upstream of two coding regions. In a case where the transcription construct is monocistronic, the transcription construct contains one promoter at an upstream of each coding region. Alternatively, of course, two transcription constructs can be prepared, that is, one for the nucleic acid construct of the present invention and the other for mRNA of CD1d. In addition to these aspects, such an aspect is possible that a WT1 gene product and CD1d are expressed as a fusion protein. This aspect provides mRNA having a specific proteolytic signal sequence (such as a T2A sequence) between the WT1 gene product and CD1d. In a cell to which such mRNA is introduced, the fusion protein is expressed and then is degraded into two proteins, so as to exhibit activities as individual proteins.

[Method for Producing Nucleic Acid Construct of the Present Invention]

The nucleic acid construct of the present invention is produced by, for example, (i) a combination of amplification, cloning, and an in vitro transcription reaction of the polynucleotide encoding the nucleic acid construct or (ii) a publicly known technique such as chemical synthesis. The following description will discuss an example of a method for producing the nucleic acid construct of the present invention.

Such a primer pair is designed that can introduce a desired mutation into cDNA of a publicly known WT1 gene. The primer pair is designed so that, for example, an N terminal of a sequence of a wild type is deleted. In this case, normally, it is not necessary to adjust the number of bases to be deleted. This is because that RNA to be transcribed in vitro does not cause a frame-shift mutation, unless a mutation as those described in [Nucleic acid construct of the present invention] occurs. By determining a sequence of template cDNA to be used, it is possible to know whether or not a frame-shift mutation has occurred therein. Therefore, before use of the template DNA, the sequence of the template DNA may be determined in accordance with a publicly known method.

A desired polynucleotide is amplified by PCR using the primer pair and the template cDNA. The polynucleotide thus amplified and a vector used for cloning are digested by use of the same restriction enzyme. The vector and polynucleotide thus digested are ligated by use of a ligase, so that the vector (transcription construct) containing the polynucleotide is obtained.

By use of the vector containing the polynucleotide of the present invention, for example, suitable *Escherichia coli* is transformed. The *Escherichia coli* thus transformed is then grown in a suitable culture medium. The vector contains, for example, a specific antibiotic resistance gene, and the culture medium used to grow the *Escherichia coli* contains the specific antibiotic. The vector is extracted from a bacterial cell with the use of a commercially available kit or the like.

The vector thus extracted is subjected to an in vitro transcription reaction with the use of a commercially available kit, with the vector being kept circular or being processed to be linear. In a case where a resulting transcription product does not have a modification such as a cap structure added to a 5' terminal and a Poly-A sequence added to a 3' terminal, the cap structure can be added to the 5' terminal of the transcription product and the poly A sequence can be added to the 3' terminal of the transcription product with the use of a commercially available kit.

The above description has given a simple discussion mainly on the method for producing the nucleic acid construct of the present invention with the use of a kit.

However, a person skilled in the art would understand that he/she can prepare by himself/herself part of the reagents used to produce the nucleic acid construct. Therefore, a person skilled in the art can produce more suitable RNA by partially altering a commercially available kit or by changing part of the reagents in accordance with a nature of RNA to be produced. Particularly, with reference to Examples described later, a person skilled in the art would sufficiently understand a technique suitable to produce the nucleic acid construct of the present invention, a reagent to be prepared, a kit to be selected, and part of those which should be changed.

EXAMPLES

Example 1

Production of RNA According to the Present Invention

Example 1-a

Cloning of Polynucleotide Encoding RNA of the Present Invention

A polynucleotide sequence of a target WT1 was obtained by PCR. Used as a template was plasmid DNA into which purchased cDNA (#SC308799, OriGene Technologies, SEQ ID NO: 3) encoding Variant D of human WT1 was inserted. Used as DNA polymerase for PCR was KOD-Plus-Ver.2 (#KOD-211, Toyobo Co., Ltd.). Oligonucleotide sequences of a primer pairs and a reaction condition of PCR were as follows.

(Primer Pair for ATG-WT1)

Forward: 5'-CCAAGCTTCCACCATGCAGGACCCG-GCTTCCACG-3' (SEQ ID NO: 5, Positions 3 to 8: a recognition sequence of the restriction enzyme HindIII; Positions 9 to 13: Kozak sequence; Positions 14 to 34: part of coding region sequence of WT1);

Reverse: 5'-CGGAATTCTCAAAGCGCCAGCTGGAG TT TGG-3' (SEQ ID NO: 6, Positions 3 to 8: a recognition sequence of the restriction enzyme EcoRI; Positions 9 to 31: part of coding region sequence of WT1).

TABLE 1

(Composition of Reaction Solution for PCR)

| | |
|---|---|
| Water | 25.6 µl |
| 10× Buffer for KOD -Plus- Ver. 2 | 4.0 µl |
| 2 mM dNTPs | 4.0 µl |
| 25 mM MgSO4 | 2.4 µl |
| Forward primer (10 µM) | 1.2 µl |
| Reverse primer (10 µM) | 1.2 µl |
| WT1 cDNA (1 ng/µl) | 0.8 µl |
| KOD -Plus- (1 U/µl) | 0.8 µl |
| Total | 40.0 µl |

An expected chain length of the amplification products of ATG-WT1 (corresponding to positions 191 to 1741 ("c" at position 191 was substituted with "a") of SEQ ID NO: 3) as the result of PCR was approximately 1580 base pairs. By agarose gel electrophoresis, it was confirmed that the chain length of the PCR product did not conflict with theoretical value. The amplification product was cloned into the plasmid pcDNA3, and the plasmid thus obtained was named pcDNA3-ATG-WT1.

(Production of Synthetic RNA of the Present Invention)

The plasmid pcDNA3-ATG-WT1 was processed to be linear by use of the restriction enzyme NotI (recognition sequence is on pcDNA3). The linear plasmid thus obtained was purified by use of QIAquick PCR Purification Kit (#28106, Qiagen) and then used as a template for RNA synthesis. As a result, desired RNA (SEQ ID NO. 4) was synthesized.

Example 2

Therapeutic Effects Targeting the WT1 Antigen by Administration of aAVC-WT1

Figure 1:
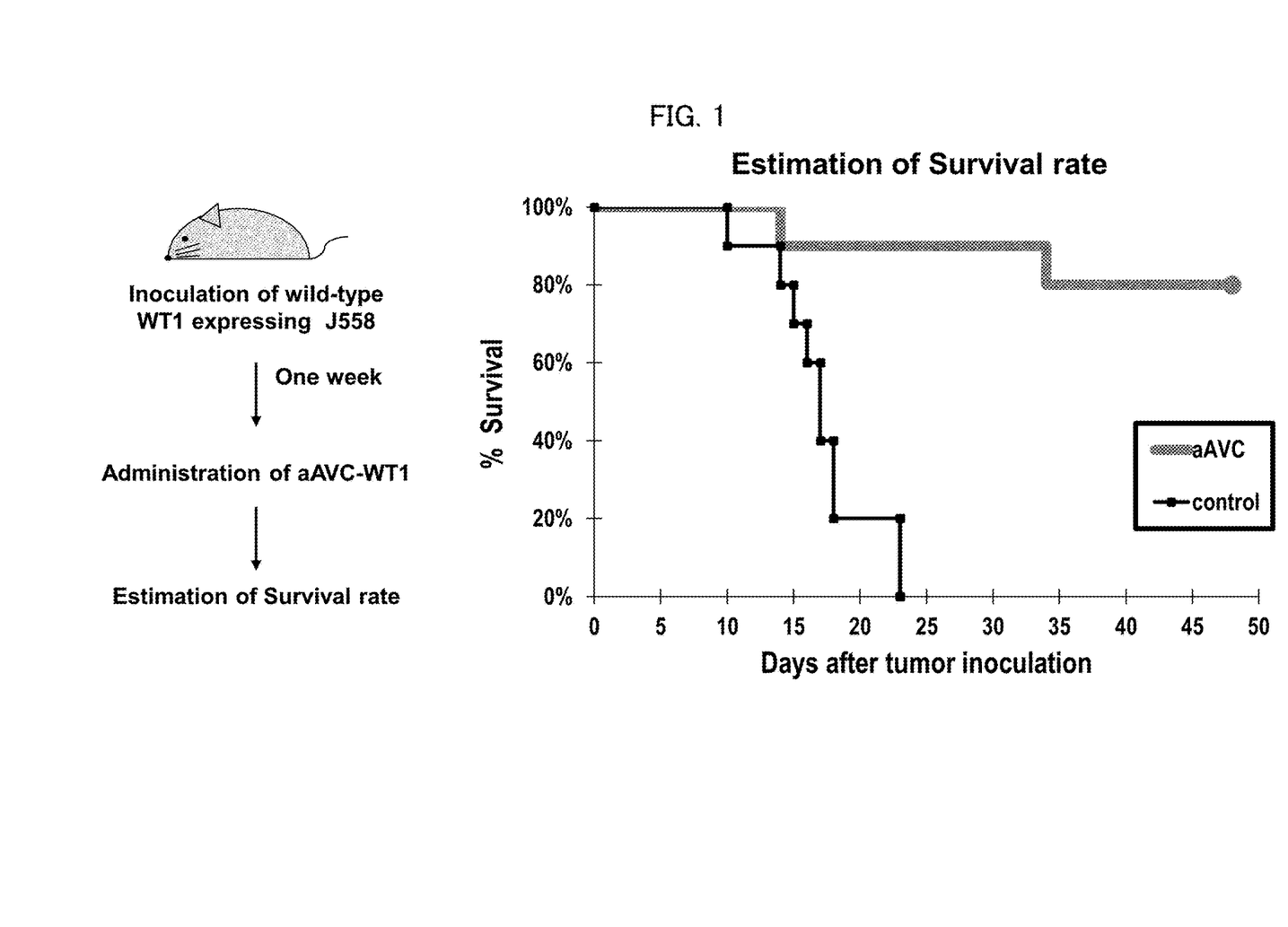
FIG. 1 is a view illustrating the procedure and results of animal experiments that assess the antitumor effects of aAVC according to Example 2. In animal experiments, mice were inoculated with $1 \times 10^6$ wild type WT1-expressing J558 cells, treated with aAVC-WT1 at day 7, and then evaluated for survival.
Figure 2:
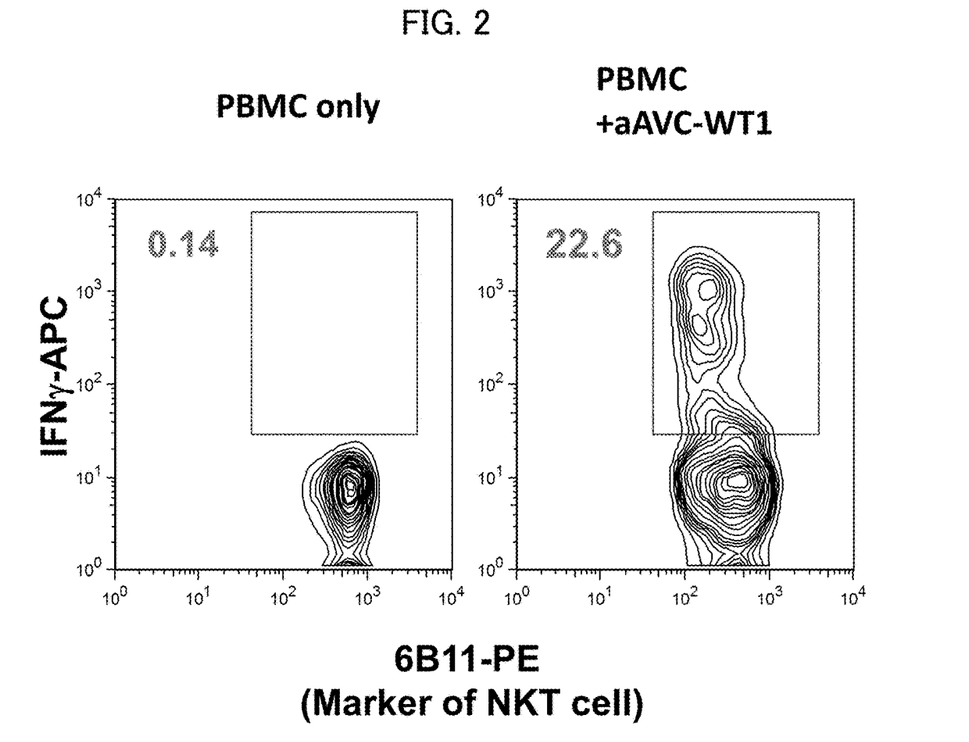
FIG. 2 is a view illustrating the results of flow cytometry that assess the ability of the aAVC to activate human NKT. For the primary NKT cell response, $1 \times 10^5$ human PBMCs were cultured alone or cocultured with 30 Gy-irradiated $1 \times 10^4$ aAVC-WT1 in the presence of GolgiPlug for 6 hours. Intracellular IFNg staining was performed.

Wilms' tumor gene WT1 encodes a protein that has been reported to be a tumor antigen in a variety of malignancies. To evaluate whether WT1 could be used in our vaccine models, we established alpha-GalCer-loaded, mCD1d mRNA and WT1 mRNA co-transfected NIH3T3 cells that is denoted mouse aAVC-WT1. The WT1 mRNA used in aAVC-WT1 had AUG as start codon that is different from wild type WT1 mRNA (CUG). The preparation of the mouse aAVC-WT1 was as follows; NIH3T3 cells resuspended in OptiMEM and RNA were transferred to a cuvette and then the cell suspension was pulsed in ECM 830 Square Wave Electroporation System (Harvard Apparatus). Pulse condition was a single 500 V, 3 ms square pulse. Immediately after electroporation, the cells were transferred to culture medium and cultured in the presence of 500 ng/mL of alpha-GalCer. The mouse aAVC-WT1 included a WT1 mRNA according to this invention (SEQ ID NO. 4), not wild type WT1 mRNA (SEQ ID NO2.). As aAVC-WT1 vaccine efficacy, we confirmed WT1-specific T-cell responses 7 days after administration of aAVC-WT1. Next, we injected mice with a WT1-expressing plasmacytoma cell line (J558-WT1) and then treated them with mouse aAVC-WT1 at day 7. In the control untreated group, all of the mice died within 30 days after inoculation with tumor cells. In contrast, 75% of the aAVC-WT1-treated mice survived more than 3 months (FIG. 1). In contrast, aAVC-WT1 therapy did not protect mice from the parental J558 or the WEHI3B leukemia cell line, demonstrating specificity of the protection. These results clearly indicated that the WT1-specific antitumor effect was generated by aAVC-WT1 treatment. The surviving mice were rechallenged with the J558-WT1 cells or WEHI3B cells more than 4 months later. As results, all of mice rechallenged with J558-WT1 cells were survived, on the other hand all of mice rechallenged with WEHI3B cells died, demonstrating the specificity of the protection. The data suggest that aAVC therapy can induce a tumor antigen-specific memory response. Next, we asked whether human NKT cells can respond to human aAVC-WT1. For this purpose, we established alpha-GalCer-loaded, hCD1d mRNA and WT1 mRNA-co-transfected HEK293 cells as human aAVC (denoted human aAVC-WT1). The preparation of the human aAVC-WT1 was as follows; HEK293 cells resuspended in OptiMEM and RNA were transferred to a cuvette and then the cell suspension was pulsed in ECM 830 Square Wave Electroporation System (Harvard Apparatus). Pulse condition was a single 500 V, 3 ms square pulse. Immediately after electroporation, the cells were transferred to culture medium and cultured in the presence of 500 ng/mL of alpha-GalCer. The human aAVC-WT1 included a WT1 mRNA according to this invention (SEQ ID NO.4), not wild type WT1 mRNA (SEQ ID NO.2). At first, we verified that CD1d and WT1 are expressed in the CD1d and WT1 co-transfected HEK293 cells. The cells contained $178.2 \pm 41.3$ µg WT1 protein/$1 \times 10^6$ cells. Human NKT cells recognized and killed the CD1d and WT1 co-transfected HEK293 cells loaded with alpha-GalCer (human aAVC-WT1), but not the cell unloaded with alpha-GalCer. Then, we examined whether NKT and T-cell responses could be induced after co-culturing PBMCs and human aAVC-WT1. As shown in FIG. 2, NKT cells expressed IFNg after a 6-hour culture with human aAVC-WT1. However they did not produce IFNg in response to the co-transfected HEK293 cells unloaded with alpha-GalCer. Also, when we cultured HLA-A24+ PBMCs derived from healthy volunteers with human aAVC-WT1, WT1-tetramer+ T cells were generated, but when we cultured the HLA-A24+ PBMCs with the control HIV peptide, no T cells specific for were observed. The human aAVC-WT1 were more effective at generating WT1-tetramer+CD8+ T cells than culture of PBMCs in the presence of WT1 peptide and IL2. Some human DCs and monocytes as DC precursor express HLA-DR and/or CD14. To confirm the importance of DCs in this system, we depleted CD14+ and DR+ cells before the co-culture, and no WT1-tetramer+CD8+ T cells were generated. Thus, aAVC-WT1 can generate human WT1-specific T cells, and this process is dependent on antigen-presenting cells, mainly DCs.

INDUSTRIAL APPLICABILITY

The present invention is expected to be applied to the biological fields and the medical fields, particularly, to treatments for tumors.

The invention claimed is:

1. A cell for immunotherapy, comprising:
    a nucleic acid sequence encoding a Wilms tumor 1 gene product or a fragment of a Wilms tumor 1 gene product, wherein the nucleic acid sequence comprises
    (i) a region encoding a gene product having positions 194 to 493 of amino acid sequence of SEQ ID NO:1 or positions corresponding to positions 194 to 493 of amino acid sequence corresponding to SEQ ID NO:1 and
    (ii) AUG as a functional start codon, wherein the AUG is connected to a 5' terminal side via 3m (m is 124-192) bases intervening between the AUG as the functional start codon and the 5' terminal side of the region, and
    a nucleic acid encoding CD1d,
    wherein the cell comprises a glycolipid recognized by an antigen receptor of NKT cell.

2. The cell of claim 1, wherein the cell is a HEK293 cell.

3. The cell of claim 1, wherein the glycolipid is alpha-GalCer.

* * * * *

SEQUENCE LISTING

```
<160> NUMBER OF SEQ ID NOS: 6

<210> SEQ ID NO 1
<211> LENGTH: 517
<212> TYPE: PRT
<213> ORGANISM: human

<400> SEQUENCE: 1

Met Gln Asp Pro Ala Ser Thr Cys Val Pro Glu Pro Ala Ser Gln His
1               5                   10                  15
```

```
Thr Leu Arg Ser Gly Pro Gly Cys Leu Gln Gln Pro Glu Gln Gly
            20                  25                  30

Val Arg Asp Pro Gly Gly Ile Trp Ala Lys Leu Gly Ala Ala Glu Ala
            35                  40                  45

Ser Ala Glu Arg Leu Gln Gly Arg Arg Ser Arg Gly Ala Ser Gly Ser
            50                  55                  60

Glu Pro Gln Gln Met Gly Ser Asp Val Arg Asp Leu Asn Ala Leu Leu
65                      70                  75                  80

Pro Ala Val Pro Ser Leu Gly Gly Gly Gly Cys Ala Leu Pro Val
                    85                  90                  95

Ser Gly Ala Ala Gln Trp Ala Pro Val Leu Asp Phe Ala Pro Pro Gly
                100                 105                 110

Ala Ser Ala Tyr Gly Ser Leu Gly Gly Pro Ala Pro Pro Ala Pro
                115                 120                 125

Pro Pro Pro Pro Pro Pro Pro His Ser Phe Ile Lys Gln Glu Pro
            130                 135                 140

Ser Trp Gly Gly Ala Glu Pro His Glu Glu Gln Cys Leu Ser Ala Phe
145                     150                 155                 160

Thr Val His Phe Ser Gly Gln Phe Thr Gly Thr Ala Gly Ala Cys Arg
                    165                 170                 175

Tyr Gly Pro Phe Gly Pro Pro Pro Ser Gln Ala Ser Ser Gly Gln
                180                 185                 190

Ala Arg Met Phe Pro Asn Ala Pro Tyr Leu Pro Ser Cys Leu Glu Ser
                195                 200                 205

Gln Pro Ala Ile Arg Asn Gln Gly Tyr Ser Thr Val Thr Phe Asp Gly
210                     215                 220

Thr Pro Ser Tyr Gly His Thr Pro Ser His His Ala Ala Gln Phe Pro
225                     230                 235                 240

Asn His Ser Phe Lys His Glu Asp Pro Met Gly Gln Gln Gly Ser Leu
                    245                 250                 255

Gly Glu Gln Gln Tyr Ser Val Pro Pro Val Tyr Gly Cys His Thr
                260                 265                 270

Pro Thr Asp Ser Cys Thr Gly Ser Gln Ala Leu Leu Leu Arg Thr Pro
                275                 280                 285

Tyr Ser Ser Asp Asn Leu Tyr Gln Met Thr Ser Gln Leu Glu Cys Met
290                     295                 300

Thr Trp Asn Gln Met Asn Leu Gly Ala Thr Leu Lys Gly Val Ala Ala
305                     310                 315                 320

Gly Ser Ser Ser Val Lys Trp Thr Glu Gly Gln Ser Asn His Ser
                325                 330                 335

Thr Gly Tyr Glu Ser Asp Asn His Thr Thr Pro Ile Leu Cys Gly Ala
                340                 345                 350

Gln Tyr Arg Ile His Thr His Gly Val Phe Arg Gly Ile Gln Asp Val
            355                 360                 365

Arg Arg Val Pro Gly Val Ala Pro Thr Leu Val Arg Ser Ala Ser Glu
            370                 375                 380

Thr Ser Glu Lys Arg Pro Phe Met Cys Ala Tyr Pro Gly Cys Asn Lys
385                     390                 395                 400

Arg Tyr Phe Lys Leu Ser His Leu Gln Met His Ser Arg Lys His Thr
                    405                 410                 415

Gly Glu Lys Pro Tyr Gln Cys Asp Phe Lys Asp Cys Glu Arg Arg Phe
                420                 425                 430

Ser Arg Ser Asp Gln Leu Lys Arg His Gln Arg Arg His Thr Gly Val
```

```
                435                 440                 445
Lys Pro Phe Gln Cys Lys Thr Cys Gln Arg Lys Phe Ser Arg Ser Asp
    450                 455                 460

His Leu Lys Thr His Thr Arg Thr His Thr Gly Lys Thr Ser Glu Lys
465                 470                 475                 480

Pro Phe Ser Cys Arg Trp Pro Ser Cys Gln Lys Lys Phe Ala Arg Ser
                485                 490                 495

Asp Glu Leu Val Arg His His Asn Met His Gln Arg Asn Met Thr Lys
            500                 505                 510

Leu Gln Leu Ala Leu
        515

<210> SEQ ID NO 2
<211> LENGTH: 3037
<212> TYPE: RNA
<213> ORGANISM: human

<400> SEQUENCE: 2
agcuggggua aggaguucaa ggcagcgccc acacccgggg gcucuccgca acccgaccgc    60 cguccgcuc  cccacuucc  cgcccucccu  cccaccuacu  cauucaccca  cccacccacc  120
cagagccggg acggcagccc aggcgcccgg gccccgccgu cccucgccg  cgauccugga   180 cuuccucuug cugcaggacc cggcuuccac gugugucccg gagccggcgu cucagcacac   240
gcuccgcucc gggccugggu gccuacagca gccagagcag cagggagucc gggacccggg   300
cggcaucugg gccaaguuag cgccgccga  ggccagcgcu gaacgucucc agggccggag   360
gagccgcggg gcguccgggu cugagccgca gcaaaugggc uccgacgugc gggaccugaa   420
cgcgcugcug cccgccgucc ccucccuggg uggcggcggc ggcugugccc ugccugugag   480
cggcgcggcg caguggggcgc cggugcugga cuuugcgccc ccgggcgcuu cggcuuacgg   540 gucguuggc  ggccccgcgc cgccaccggc uccgccgcca ccccgccgc  cgccgccuca   600 cuccuucauc aaacaggagc cgagcugggg cggcgcggag ccgcacgagg agcagugccu   660
gagcgccuuc acuguccacu uuuccggcca guucacuggc acagccggag ccugucgcua   720 cggggcccuuc gguccuccuc cgcccagcca ggcgucaucc ggccaggcca ggauguuucc   780
uaacgcgccc uaccugccca gcugccucga gagccagccc gcuauucgca aucagggua   840 cagcacgguc accuugacg  ggacgccag  cuacggucac acgcccucgc accaugcggc   900 gcaguuc ccc aaccacucau ucaagcauga ggaucccaug ggccagcagg gcucgcuggg   960
ugagcagcag uacucgggcg cgccccggu  cuauggcugc  cacaccccca ccgacagcug  1020
caccggcagc caggcuuugc ugcugaggac gcccuacagc agugacaauu uauaccaaau  1080
gacaucccag cuugaaugca ugaccuggaa ucagaugaac uuaggagcca ccuuaaaggg  1140
aguugcugcu gggagcucca gcucagugaa auggacagaa gggcagagca ccacagcac   1200 agggacgag  agcgauaacc acacaacgcc caucccucgc ggagcccauu acagaauaca  1260
cacgcacggu gucuucagag gcauucagga ugugcgacgu gugccuggag uagccccgac  1320
ucuuguacgg ucggcaucug agaccaguga gaaacgcccc uucaugugug cuuacccagg  1380
cugcaauaag agauauuuua agcuguccca cuuacagaug cacagcagga agcacacugg  1440
ugagaaacca uaccagugug acuucaagga cugugaacga gguuucucu  guucagacca  1500 gcucaaaaga caccaaagga gacauacagg ugugaaacca uuccagugua aacuuguca   1560 gcgaaaguuc uccggguccg accaccugaa gacccacacc aggacucaua cagguaaaac  1620
```

```
aagugaaaag cccuucagcu gucgguggcc aaguugucag aaaaaguuug cccggucaga    1680
ugaauuaguc cgccaucaca acaugcauca gagaaacaug accaaacucc agcuggcgcu    1740
uugaggggu cucccucgggg accguucagu gucccaggca gcacagugug ugaacugcuu    1800
ucaagucuga cucuccacuc cuccucacua aaaaggaaac uucaguugau cuucuucauc    1860
caacuuccaa gacaagauac cggugcuucu ggaaacuacc aggugugccu ggaagaguug    1920
gucucugccc ugccuacuuu uaguugacuc acaggcccug gagaagcagc uaacaaugu c   1980
ugguuaguua aaagcccauu gccauuuggu guggauuuuc uacuguaaga agagccauag    2040
cugaucaugu cccccugacc cuucccuucu uuuuuaugc ucguuuucgc uggggaugga     2100
auuauuguac cauuuucuau cauggaauau uuauaggcca gggcaugugu auguguucugc  2160
uaauguaaac uuugucaugg uuccauuua cuaacagcaa cagcaagaaa uaaaucagag     2220
agcaaggcau cggggguga a ucuugucuaa cauucccgag gucagccagg cugcuaaccu   2280
ggaaagcagg auguaguucu gccaggcaac uuuuaaagcu caugcauuuc aagcagcuga    2340
agaaaaaauc agaacuaacc aguaccucug uauagaaauc uaaaagaauu uuaccauuca    2400
guuaauucaa ugugaacacu ggcacacugc ucuuaagaaa cuaugaagau cugagauuuu    2460
uuuguguaug uuuuugacuc uuuugagugg uaacauaug ugucuuuaua gauguacaua    2520
ccuccuugca caauggagg ggaauucauu uucaucacug ggagugcccu uaguguauaa    2580
aaaccaugcu gguauauggc uucaaguguu aaaaugaaa gugacuuuaa aagaaaauag    2640
gggauggucc aggaucucca cugauaagac uguuuuuaag uaacuuaagg accuuugggu   2700
cuacaaguau auguga aaaa aaugagacuu acugggugag gaaauccauu guuuaaagau  2760
ggucgugugu gugugugugu gugugugugu gugugugug uguuguguuu uguuuuuaa     2820
gggagggaau uuauuauuua ccguugcuug aaauuacugu guaauauauau gucugauaau  2880
gauuugcucu uugacaacua aaauuaggac uguauaagua cuagaugcau cacugggugu   2940
ugaucuuaca agauauugau gauaacacuu aaaauuguaa ccugcauuuu ucacuuugcu   3000
cucaauuaaa gucuauucaa aaggaaaaaa aaaaaaa                            3037
```

<210> SEQ ID NO 3
<211> LENGTH: 3037
<212> TYPE: DNA
<213> ORGANISM: human

<400> SEQUENCE: 3

```
agctggggta aggagttcaa ggcagcgccc acacccgggg gctctccgca acccgaccgc     60
ctgtccgctc ccccacttcc cgccctccct cccacctact cattcaccca cccacccacc    120
cagagccggg acggcagccc aggcgccggg gccccgccgt ctcctcgccg cgatcctgga    180
cttcctcttg ctgcaggacc cggcttccac gtgtgtcccg gagccggcgt ctcagcacac    240
gctccgctcc gggcctgggt gcctacagca gccagagcag cagggagtcc ggacccgggg   300
cggcatctgg gccaagttag cgccgccga ggccagcgct gaacgtctcc agggccggag    360
gagccgcggg gcgtccgggt ctgagccgca gcaaatgggc tccgacgtgc gggacctgaa    420
cgcgctgctg cccgccgtcc cctccctggg tggcggcggc ggctgtgccc tgcctgtgag    480
cggcgcggcg cagtgggcgc cggtgctgga cttttgcgccc ccggggcgctt cggcttacgg   540
gtcgttgggc ggccccgcgc cgccaccggc tccgccgcca cccccgccgc cgccgcctca    600
ctccttcatc aaacaggagc cgagctgggg cggcgcggag ccgcacgagg agcagtgcct    660
gagcgccttc actgtccact tttccggcca gttcactggc acagccggag cctgtcgcta    720
```

```
cgggcccttc ggtcctcctc cgcccagcca ggcgtcatcc ggccaggcca ggatgtttcc    780
taacgcgccc tacctgccca gctgcctcga gagccagccc gctattcgca atcagggtta    840
cagcacggtc accttcgacg ggacgcccag ctacggtcac acgccctcgc accatgcggc    900
gcagttcccc aaccactcat tcaagcatga ggatcccatg ggccagcagg gctcgctggg    960
tgagcagcag tactcggtgc cgccccggt ctatggctgc cacacccca ccgacagctg     1020
caccggcagc caggctttgc tgctgaggac gccctacagc agtgacaatt tataccaaat    1080
gacatcccag cttgaatgca tgacctggaa tcagatgaac ttaggagcca ccttaaaggg    1140
agttgctgct gggagctcca gctcagtgaa atggacagaa gggcagagca accacagcac    1200
agggtacgag agcgataacc acacaacgcc catcctctgc ggagcccaat acagaataca    1260
cacgcacggt gtcttcagag gcattcagga tgtgcgacgt gtgcctggag tagccccgac    1320
tcttgtacgg tcggcatctg agaccagtga gaaacgcccc ttcatgtgtg cttacccagg    1380
ctgcaataag agatatttta agctgtccca cttacagatg cacagcagga agcacactgg    1440
tgagaaacca taccagtgtg acttcaagga ctgtgaacga aggttttctc gttcagacca    1500
gctcaaaaga caccaaagga gacatacagg tgtgaaacca ttccagtgta aaacttgtca    1560
gcgaaagttc tcccggtccg accacctgaa gacccacacc aggactcata caggtaaaac    1620
aagtgaaaag cccttcagct gtcggtggcc aagttgtcag aaaaagtttg cccggtcaga    1680
tgaattagtc cgccatcaca acatgcatca gagaaacatg accaaactcc agctggcgct    1740
ttgaggggtc tccctcgggg accgttcagt gtcccaggca gcacagtgtg tgaactgctt    1800
tcaagtctga ctctccactc ctcctcacta aaaaggaaac ttcagttgat cttcttcatc    1860
caacttccaa gacaagatac cggtgcttct ggaaactacc aggtgtgcct ggaagagttg    1920
gtctctgccc tgcctacttt tagttgactc acaggccctg gagaagcagc taacaatgtc    1980
tggttagtta aaagcccatt gccatttggt gtggattttc tactgtaaga gagcccatag    2040
ctgatcatgt ccccctgacc cttcccttct tttttatgc tcgttttcgc tggggatgga    2100
attattgtac cattttctat catggaatat ttataggcca gggcatgtgt atgtgtctgc    2160
taatgtaaac tttgtcatgg tttccattta ctaacagcaa cagcaagaaa taatcagag    2220
agcaaggcat cgggggtgaa tcttgtctaa cattcccgag gtcagccagg ctgctaacct    2280
ggaaagcagg atgtagttct gccaggcaac ttttaaagct catgcatttc aagcagctga    2340
agaaaaaatc agaactaacc agtacctctg tatagaaatc taaaagaatt ttaccattca    2400
gttaattcaa tgtgaacact ggcacactgc tcttaagaaa ctatgaagat ctgagatttt    2460
tttgtgtatg ttttttgactc ttttgagtgg taatcatatg tgtctttata gatgtacata    2520
cctccttgca caaatggagg ggaattcatt ttcatcactg ggagtgtcct tagtgtataa    2580
aaaccatgct ggtatatggc ttcaagttgt aaaaatgaaa gtgactttaa aagaaaatag    2640
gggatggtcc aggatctcca ctgataagac tgttttaag taacttaagg acctttgggt     2700
ctacaagtat atgtgaaaaa aatgagactt actgggtgag gaaatccatt gtttaaagat    2760
ggtcgtgtgt gtgtgtgtgt gtgtgtgtgt gtgtgtgttg tgttgtgttt tgttttttaa    2820
gggagggaat ttattattta ccgttgcttg aaattactgt gtaaatatat gtctgataat    2880
gatttgctct ttgacaacta aaattaggac tgtataagta ctagatgcat cactgggtgt    2940
tgatcttaca agatattgat gataacactt aaaattgtaa cctgcatttt tcactttgct    3000
ctcaattaaa gtctattcaa aaggaaaaaa aaaaaaa                             3037
```

```
<210> SEQ ID NO 4
<211> LENGTH: 1551
<212> TYPE: RNA
<213> ORGANISM: human

<400> SEQUENCE: 4
augcaggacc cggcuuccac gugugucccg agccggcgu cucagcacac gcuccgcucc      60
gggccugggu gccuacagca gccagagcag cagggaguc gggacccggg cggcaucugg     120
gccaaguuag gcgccgccga ggccagcgcu gaacgucucc agggccggag gagccgcggg    180
gcguccgggu cugagccgca gcaaaugggc uccgacgugc gggaccugaa cgcgcugcug    240 cccgccguc ccucccuggg uggcggcgg ggcugugccc ugccugugag cggcgcggcg      300
cagugggcgc cggugcugga cuuugcgccc ccggggcguu cggcuuacgg gucguuuggc    360
ggccccgcgc cgccaccggc uccgccgcca ccccgccgc cgccgccuca ucccuucauc     420
aaacaggagc cgagcugggg cggcgcggag ccgcacgagg agcagugccu gagcgccuuc    480
acuguccacu uuccggcca guucacuggc acagccggag ccugucgcua cgggcccuuc    540
gguccuccuc cgcccagcca ggcgucaucc ggcgcaggcca ggauguuucc uaacgcgccc   600
uaccugccca gcugccucga gagccagccc gcuauucgca aucaggguua cagcacgguc    660
accuucgacg ggacgccag cuacggcac acgcccucgc accaugcggc gcaguucccc      720
aaccacucau caagcauga ggaucccaug ggccagcagg gcucgcuggg ugagcagcag     780
uacucggugc cgccccgu cuaggcugc cacacccca ccgacagcug caccggcagc        840
caggcuuugc ugcugaggac gcccuacagc agugacaauu uauaccaaau gacauccgag    900
cuugaaugca ugaccuggaa ucagaugaac uuaggagcca ccuuaaaggg aguugcugcu    960
gggagcucca gcuagugaa auggacagaa ggcagagca ccacagcac agguacgag      1020 agcgauaacc acacaacgcc caucccucgc ggagcccaau acagaauaca cacgcacgu    1080 gucuucagag gcauucagga ugugcgacgu gugccuggaa uagcccccgac ucuuguacgg    1140 ucggcaucug agaccaguga gaaacgcccc ucaugugug cuuacccagg cugcaauaag    1200
agauauuuua agcuguccca cuuacagaug cacagcagga agcacacugg ugagaaacca    1260
uaccagugug acuucaagga cuguguacga agguuuccuc guucagacca gcucaaaaga    1320
caccaaagga gacauacagg ugugaaacca uuccagugua aaacuugucg gcgaagauuc    1380
ucccgguccg accaccugaa gacccacacc aggacucaua cagguaaaac aagugaaaag    1440
cccuucagcu gucgguggcc aaguugucag aaaaaguuug cccggucaga ugaauuaguc    1500
cgccaucaca acauggcauc gagaaacaug accaaacucc agcuggcgcu u             1551

<210> SEQ ID NO 5
<211> LENGTH: 34
<212> TYPE: DNA
<213> ORGANISM: Artificial Sequence
<220> FEATURE:
<223> OTHER INFORMATION: Synthetic primer

<400> SEQUENCE: 5
ccaagcttcc accatgcagg acccggcttc cacg                                    34

<210> SEQ ID NO 6
<211> LENGTH: 31
<212> TYPE: DNA
<213> ORGANISM: Artificial Sequence
<220> FEATURE:
<223> OTHER INFORMATION: Synthetic primer
```

```
<400> SEQUENCE: 6
cggaattctc aaagcgccag ctggagtttg g                                31
```